United States Patent
Wong et al.

(10) Patent No.: US 7,186,930 B1
(45) Date of Patent: Mar. 6, 2007

(54) BUTTONLESS HOUSEHOLD SCALE

(75) Inventors: Anson Wong, Boca Raton, FL (US); Alejandro Herrera, Boca Raton, FL (US)

(73) Assignee: Sunbeam Products, Inc, Boca Raton, FL (US)

(*) Notice: Subject to any disclaimer, the term of this patent is extended or adjusted under 35 U.S.C. 154(b) by 0 days.

(21) Appl. No.: 11/312,822

(22) Filed: Dec. 20, 2005

(51) Int. Cl.
*A61B 5/05* (2006.01)
*G01G 19/414* (2006.01)
*G01G 19/44* (2006.01)

(52) U.S. Cl. .............................. 177/25.13; 177/25.19; 600/547

(58) Field of Classification Search .. 177/25.11–25.17, 177/25.19; 600/547
See application file for complete search history.

(56) References Cited

U.S. PATENT DOCUMENTS

| | | | |
|---|---|---|---|
| 3,547,212 A | 12/1970 | Gursin | |
| 3,967,690 A | 7/1976 | Northcutt | |
| 4,082,153 A | 4/1978 | Provi | |
| 4,303,139 A | 12/1981 | Hino | |
| 4,318,447 A | 3/1982 | Northcutt | |
| 4,363,028 A | 12/1982 | Bosnak | |
| 4,412,591 A * | 11/1983 | Reichmuth et al. ............. 177/1 |
| 4,773,492 A | 9/1988 | Ruzumna | |
| 5,000,275 A * | 3/1991 | Bullivant ................. 177/210 R |
| 5,750,937 A * | 5/1998 | Johnson et al. ........... 177/25.11 |
| 6,038,465 A | 3/2000 | Melton | |
| 6,369,338 B1 | 4/2002 | Kimura | |
| 6,472,617 B1 * | 10/2002 | Montagnino ................. 177/126 |
| 6,538,215 B2 | 3/2003 | Montagnino | |
| 6,541,714 B2 | 4/2003 | Montagnino | |
| 6,563,059 B2 * | 5/2003 | Lee ............................ 177/177 |
| 6,583,369 B2 | 6/2003 | Montagnino | |
| 6,844,506 B2 | 1/2005 | Nuesch | |
| 6,900,396 B2 * | 5/2005 | Murdter .................... 177/25.13 |
| 2004/0118664 A1 | 6/2004 | DePue | |
| 2004/0129463 A1 | 7/2004 | Carlucci | |
| 2004/0222026 A1 | 11/2004 | Kohn | |

* cited by examiner

Primary Examiner—Randy W. Gibson
(74) Attorney, Agent, or Firm—Lawrence J. Shurupoff

(57) ABSTRACT

A digital scale includes a display screen and a buttonless top platform. A controller is operatively associated with the display screen and the platform. Contact with the scale platform alone allows a user of the scale to power the scale, determine a mode of operation of the scale, and identify a user of the scale. Additionally the scale has a first mode of operation providing a reading of the user's weight and a second mode of operation providing an attribute that is dependent upon a weight of an identified user.

22 Claims, 10 Drawing Sheets

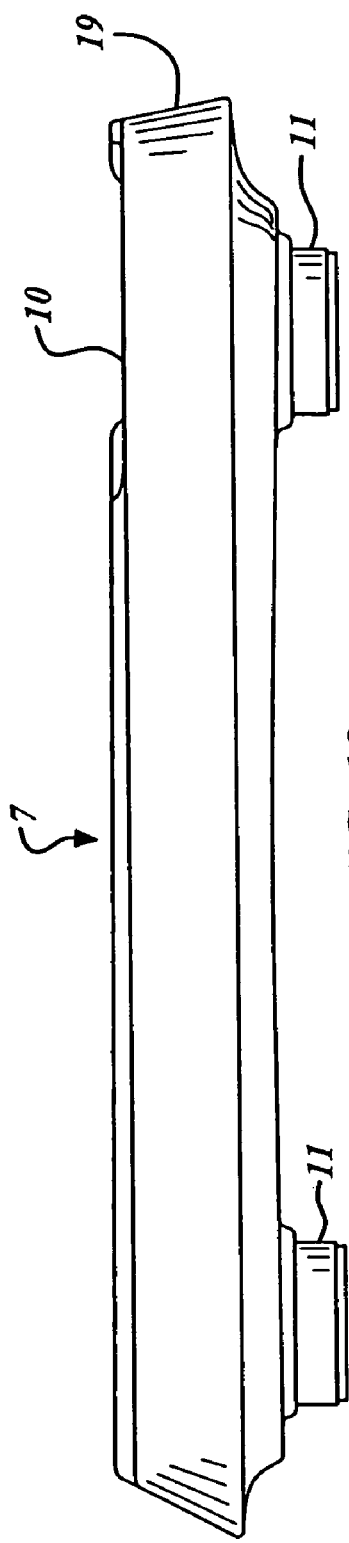
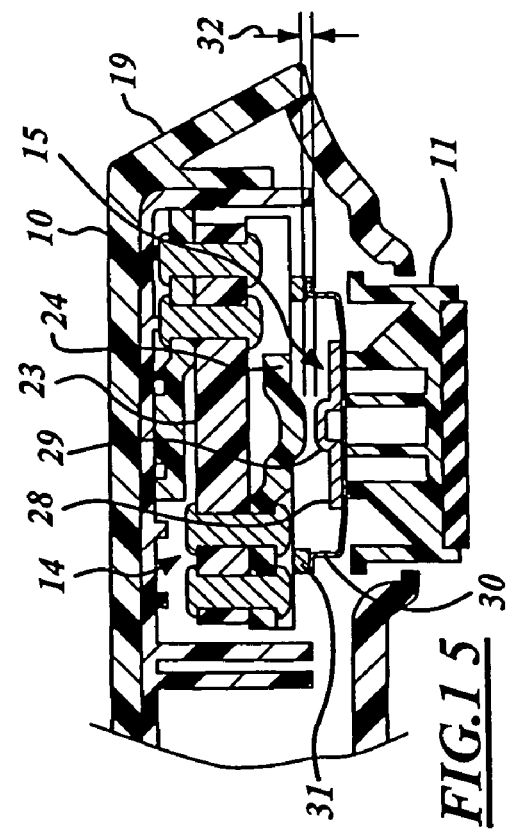
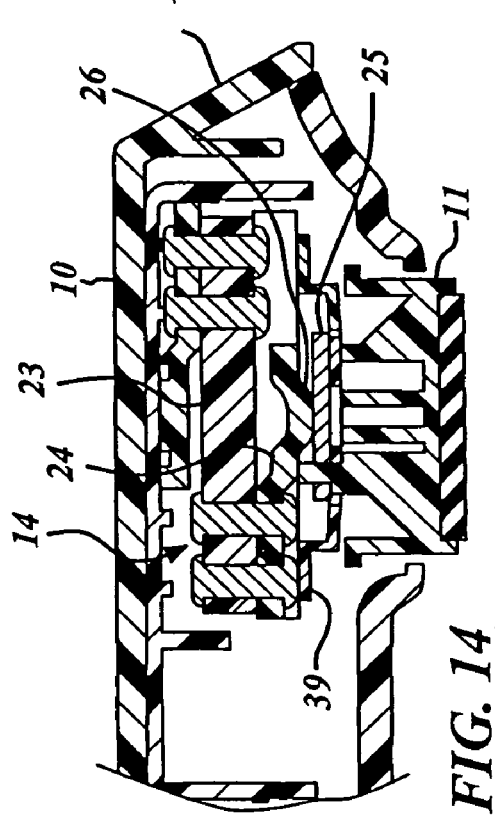

BUTTONLESS HOUSEHOLD SCALE

FIELD OF THE INVENTION

The present invention relates in general to household or bathroom scales for monitoring bodyweight.

BACKGROUND OF THE INVENTION

It is desirable to provide a household scale that is aesthetically pleasing by eliminating buttons on the scale. This improves not only the look of a scale, but also its feel, as a totally smooth surface is presented to one's feet.

SUMMARY OF THE INVENTION

The present invention provides a household body weight scale including a display screen and a buttonless top and side platform. A controller is operatively associated with the display screen and the platform. Physical contact with the scale platform alone, rather than through buttons or switches, allows a user of the scale to turn on and power the scale, determine a mode of operation of the scale, and identify a particular user of the scale. The scale has a first mode of operation providing a reading of the user's weight and a second mode of operation providing an attribute that is dependent upon a weight of an identified user.

Other features of the invention will become more apparent to those skilled in the art as the invention is further revealed in the accompanying drawings and detailed description of the invention.

BRIEF DESCRIPTION OF THE DRAWINGS

FIG. 13 is a side elevation view of the scale shown in FIG. 11.

FIG. 14 is an enlarged sectional view of the scale shown in FIG. 12 taken along a section line 14—14.

FIG. 15 is an enlarged sectional view of the scale shown in FIG. 12 taken along a section line 15—15.

DETAILED DESCRIPTION OF THE INVENTION

Figure 1:
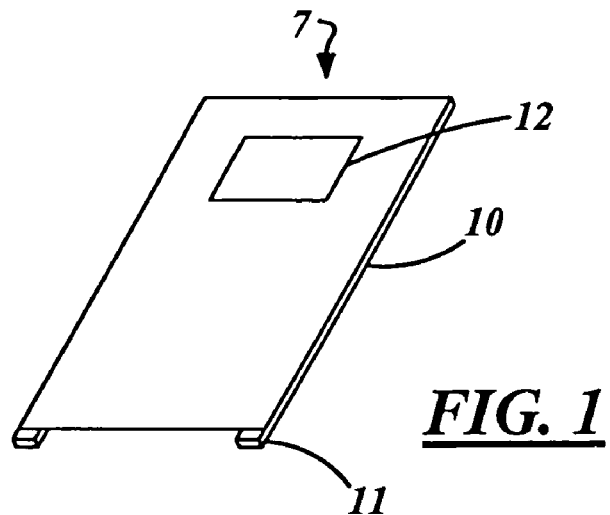
FIG. 1 is a schematic view of a preferred embodiment scale of the present invention.
Figure 2:
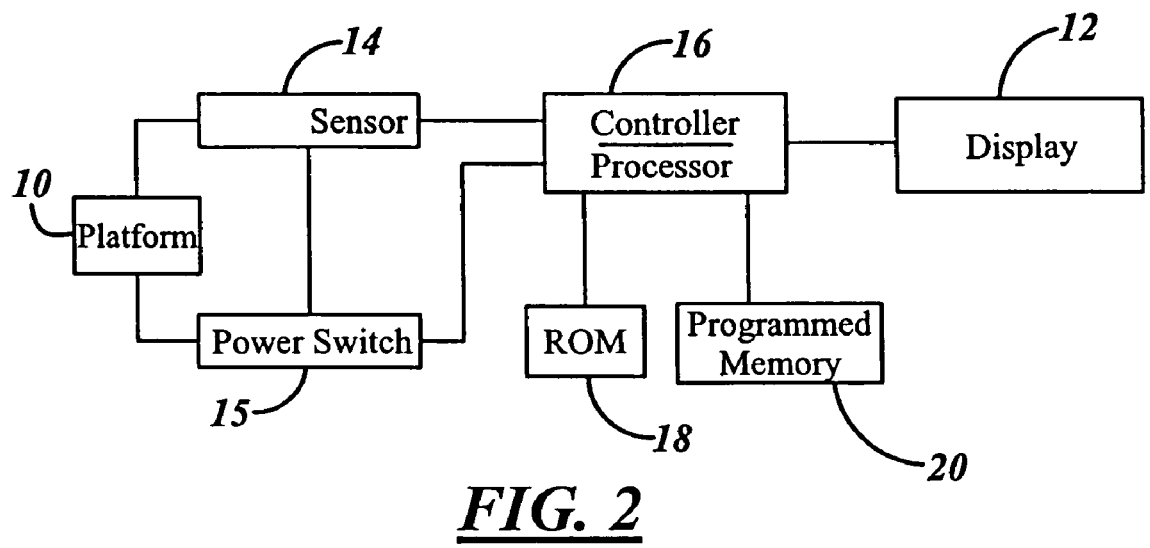
FIG. 2 is a schematic electrical diagram of the scale shown in FIG. 1.
Figure 10:
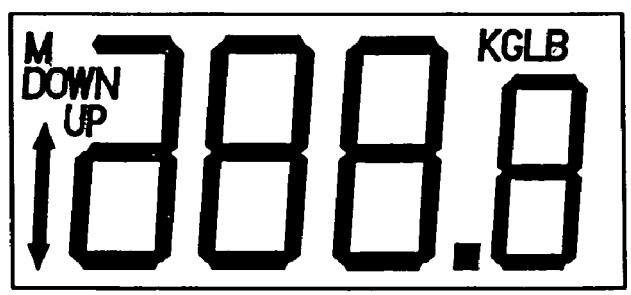
FIG. 10 is a schematic illustration of a display used in the scale shown in FIG. 1 with the process flow chart of FIGS. 3 and 4.
Figure 3:
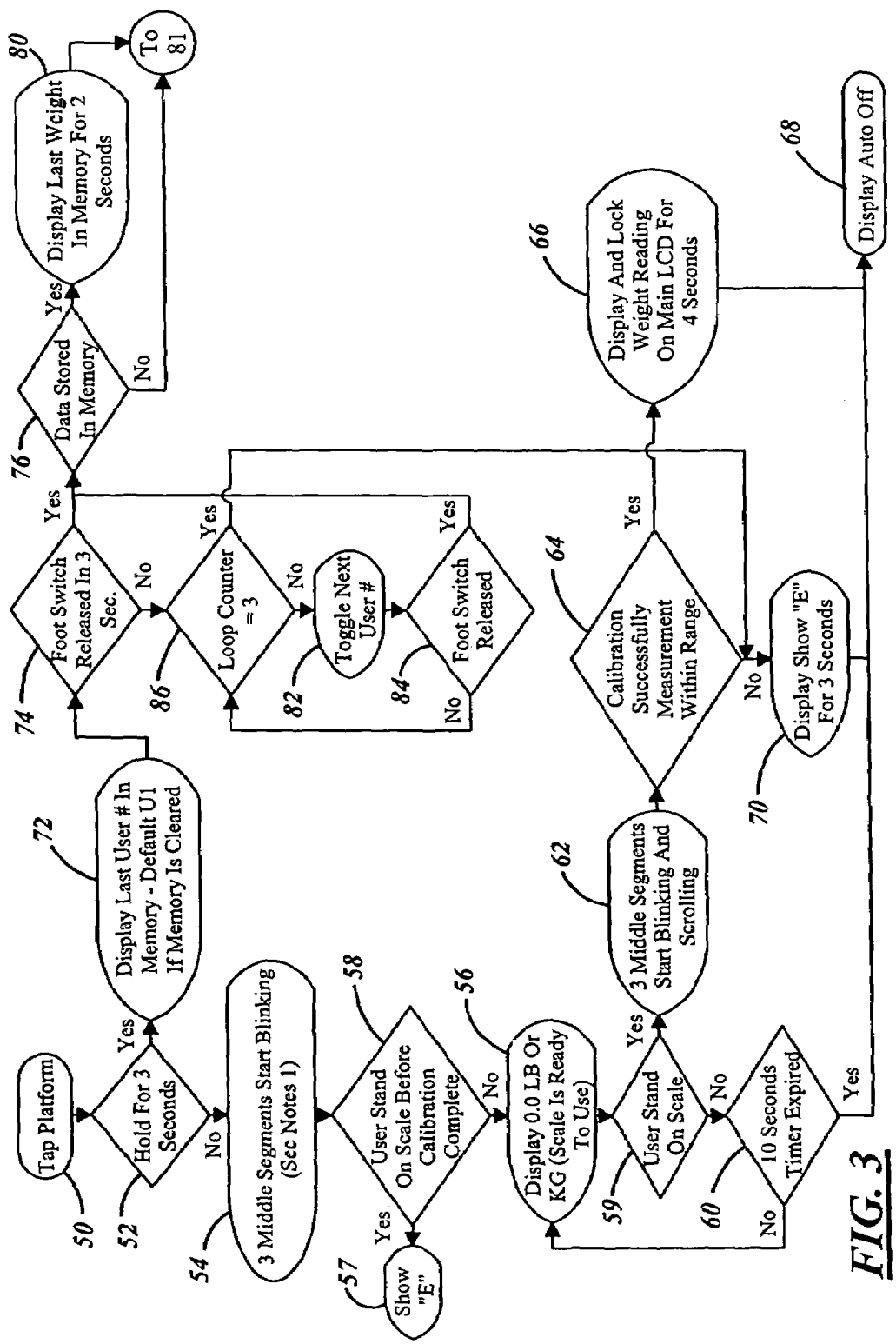
FIG. 3 is a process flow chart of a weight only mode of operation of the scale shown in FIG. 1.

Referring to FIGS. 1 and 2, a digital weight scale 7 of the present invention has a platform 10 supported on stands 11. A display 12 is provided to convey a reading to a user. Referring additionally to FIGS. 2, 3, and 10, the platform 10 is operatively associated with foot or power switch(es) 15 and load cell(s) or sensor(s) 14. The power switch 15 and sensor 14 are operatively connected with a controller or microprocessor 16. The controller or microprocessor 16 (hereinafter referred to as the controller processor) is operatively connected with the display 12, a read only memory 18, and a programmable memory 20.

The scale 7 can be powered by a battery electrical source. The read only memory 18 and the programmable memory 20 can be separate components or joined with the controller processor 16.

The display 12 can be a multiple segment LED display or LCD display. As shown in FIG. 10, display 12 is a LCD with multiple digit/numbers, up and down arrows and English (lb) and metric (kg) weight markings.

Referring additionally to FIGS. 11–15, the platform 10 has an integral side 19. The bottom of the scale 7 has a switch 22 to select English or metric units for the display readings. The scale 7 has a sensor 14 associated with each front and rear stand 11. Each sensor 14 has a load cell assembly that includes a cantileverly supported strain gauge beam 23 and an arch plate 24. In FIG. 14, a flat support plate 25 faces a valley 26 of the arch plate 24. A plastic W-spring 39 supports the support plate 25 against the arch plate valley 26. When a user steps onto the platform 10, the beam 23 is stressed causing a strain gauge (not shown) connected with the beam 23 to send a signal to the controller processor 16. The controller processor 16 interprets the collective signals from the four sensors 14 to determine the user's weight.

In FIG. 15, each of the two rearward stands 11 are additionally associated with a foot switch 15. The foot switch 15 has a support plate 28 with a crown 29. A metal W-spring 30 supports a plastic link plate 31. The plastic link plate 31 supports the sensor 14 in a manner to maintain a gap 32 of approx 0.4 mm between the arch plate 24 and the support plate crown 29. A tap on the platform 10 on its top or side 19 causes the arch plate 24 to be pushed down to close the gap 32 electrically contacting the crown 29, to activate the foot switch 15. As previously mentioned, the scale 7 has a foot switch 15 associated with each rear stand 11. Accordingly, to activate the foot switch 15 a user taps the platform 10 about the rear portion of the scale 7. If desired, foot switches 15 can be added to all of the stands 11 allowing the foot switch 15 to be activated from any location of the platform 10.

Referring to FIG. 3, beginning with operation 50, a user of the scale 7 uses their feet to contact the scale platform 10 by tapping it at a in proximity to one of the foot switches 15 thereby causing the scale 7 to be powered on. In operation 52, the user decides in what mode to operate the scale 7. If the user wants read their weight, they contact the platform 10 by holding their foot on the scale for less than three seconds. In operation 54 three middle segments of the display 12 will blink. During the time that the display 12 is blinking in operation 54, the scale 7 calibrates itself. In operation 56, after the scale 7 has been calibrated, the display 12 shows 00 to indicate to the user that the scale 7 is ready for use. If the user stands on the scale 7 before calibration is complete, as shown in operation 58, the display shows an error message "E" (operation 57). The user then has to go back to the operation 50. If the user stands up upon the scale 7 in operation 59 before the expiration of 10 seconds (after completion of scale calibration), as timed in operation 60, the three middle segments of the display 12 blink and scroll as represented by operation 62. Typically, the scale 7 has a range of weights between 45 lb and 400 lb wherein the scale measures the weight of the user accurately. If the weight measurement of the user is within the limits of accurate scale usage in operation 64, the display 12 displays the weight reading in operation 66. The display of the weight reading occurs for a predetermined time as shown in operation 66, 4 seconds. After the display of weight reading in operation 66, the controller processor 16 commands the display 12 and power switch 15 to shut off in operation 68. If in operation 64 the weight measurement is outside of the bounds of accurate weight measurement of the scale 7, the display 12 provides an "E" for three seconds (operation 70). At the conclusion of three seconds of the error message, the controller processor 16 commands the power switch 15 and display 12 to shut off (operation 68).

Returning to operation 52, if it is desired to operate the scale 7 in another mode wherein the user's weight and weight loss or gain are provided, the user holds their foot on the scale platform 10 for three seconds or longer after tapping the platform 10. The display 12 then reveals the last identified person who used the scale 7 by displaying their user number in operation 72. A default value for operation 72 will be 1. If the user removes their foot from the platform 10 before three additional seconds (operation 74), the controller processor 16 then proceeds to operation 76. In operation 76 the controller processor 16 queries the programmable memory 20 to see if the user (as identified by their user number, e.g. 1, 2, 3, etc.) has used the scale 7 before. If the user has used the scale 7 before, their prior weight recording is displayed for two seconds in operation 80.

For example, if the identified user is number 3, in operation 74 the user holds their foot on the platform 10 for three seconds. This causes the controller processor 16 to toggle the display 12 to the next higher user number in operation 82. In operation 84, the user releases their foot from the platform 10 to designate the next higher user number. Alternatively, the user keeps their foot on the platform 10 to go to a loop counter operation 86 to cause the display 12 to increase the user number. As shown in FIG. 3, the above noted action can continue for at least three additional user numbers. If the user maintains their foot on the platform 10 beyond the highest available number of cycles of the loop counter, the controller processor 16 proceeds to operation 70 to display an error message before shutting off under operation 68. As will be apparent to those skilled in the art, the loop counter of operation 86 may be increased to accommodate an increased amount of identified users for the scale 7, if desired. After the user number has been set to the desired user number, the controller processor 16 queries the programmable memory 20 as previously described in operation 76.

Figure 4:
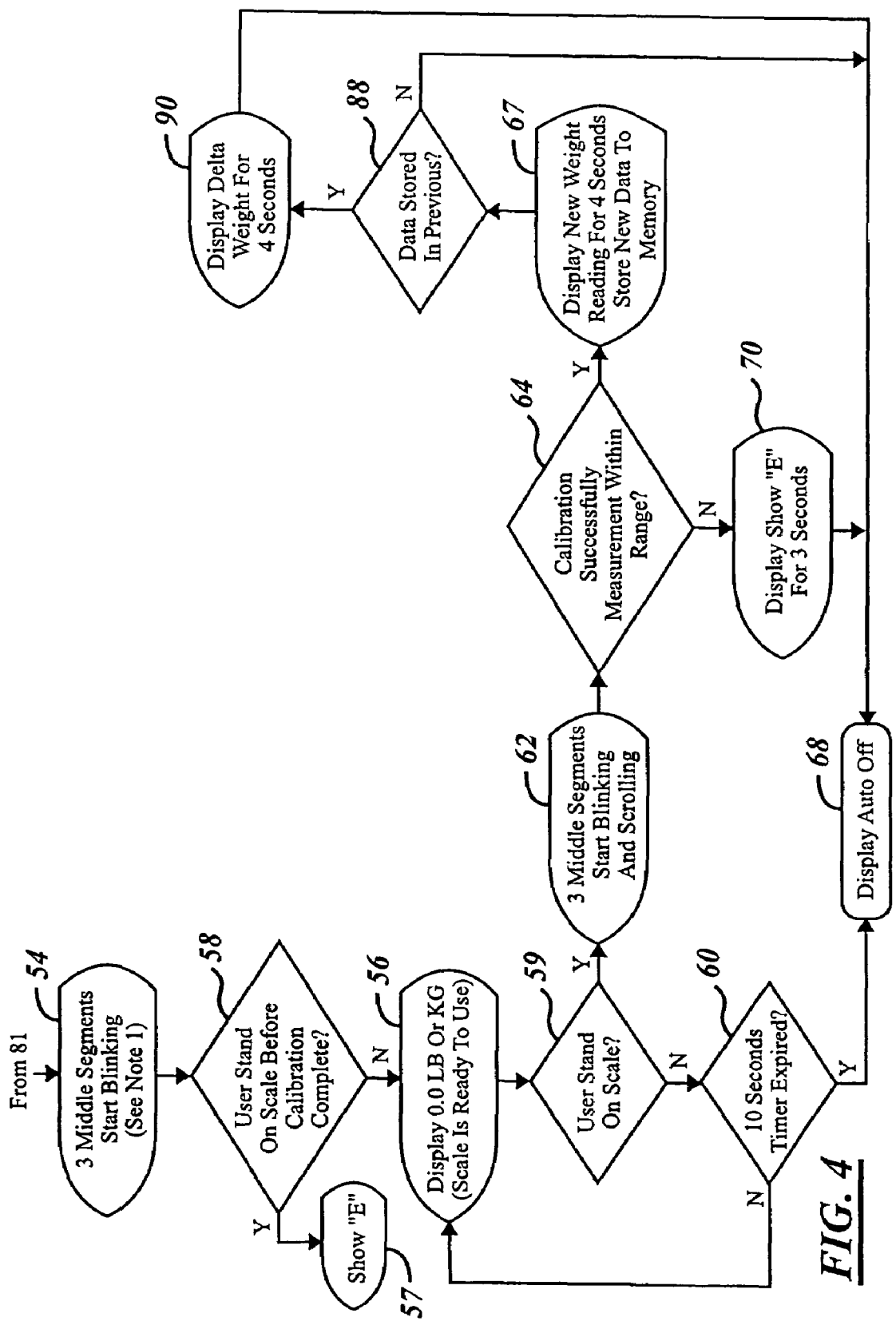
FIG. 4 is a process flow chart of a weight plus a weight dependent attribute mode of operation of the scale shown in FIG. 1.

From operation 76, regardless of whether or not the identified user has had a prior recording weight taken by the scale 7, the controller processor 16 proceeds to operation 81. As shown in FIG. 4 operation 81 loops back to operation 54. Operation 54 proceeds on as previously described for the weight only mode of operation until operation 67. In operation 67, the new weight reading is displayed for 4 seconds. In operation 67, the controller processor 16 also stores the weight reading in the programmable memory 20. In operation 88, the controller processor 16 queries the programmable memory 20 if there is data stored for this identified user. If no prior weight recording data exist for the identified user, the controller processor 16 goes to operation 68 for display 12 shut off. However if there is a prior weight recording for the identified user, a differential or delta weight value from the prior weight reading is processed and displayed in operation 90. After the delta weight has been displayed, the controller processor 16 then goes to the shut off operation 68.

Referring to FIGS. 5–9, an alternate embodiment of the present invention is presented wherein the scale 7 can additionally provide measurement reading for the percentage of body fat and the percentage of body hydration. Body fat and water hydration are attributes that are dependent upon weight, age, gender and height of an individual. The major components in the alternate embodiment are the same as or identical to those described in regards to FIG. 2, with the exception of certain additions in the controller processor 16, read-only memory 18, programmable memory 20, and display 12. The display 12 is modified to have a top row and a bottom row. The top row displays a four digit number plus a decimal point, an individual icon, an individual number, a foot and inch or cm height marking, as well as small print text to indicate English or metric units for weight readings. The top row can also provided text to indicate height and gender.

The display bottom row has screens for letters and digits, percentage markers and text indicating body fat or water which is short for water hydration percentage and age. Additionally, the bottom row has an icon to indicate the gender of an identified scale user.

Figure 6:
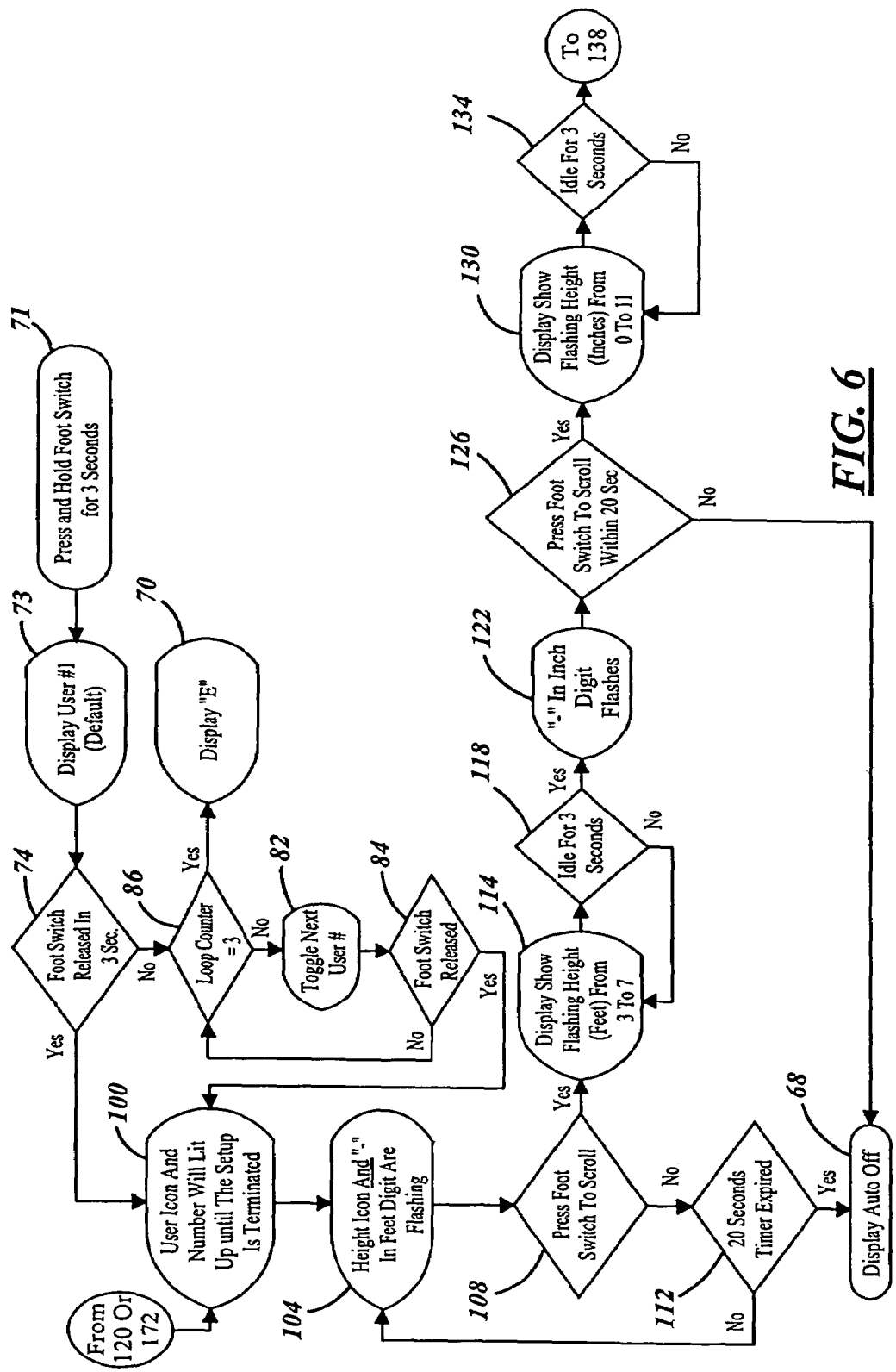
FIGS. 6 and 7 are a process flow chart of an initial set up of a scale as shown in FIG. 1 having a mode of operation providing an identified user's weight and an attribute of the identified user that is both dependent upon the identified user's weight and a unique quality of the identified user.
Figure 7:
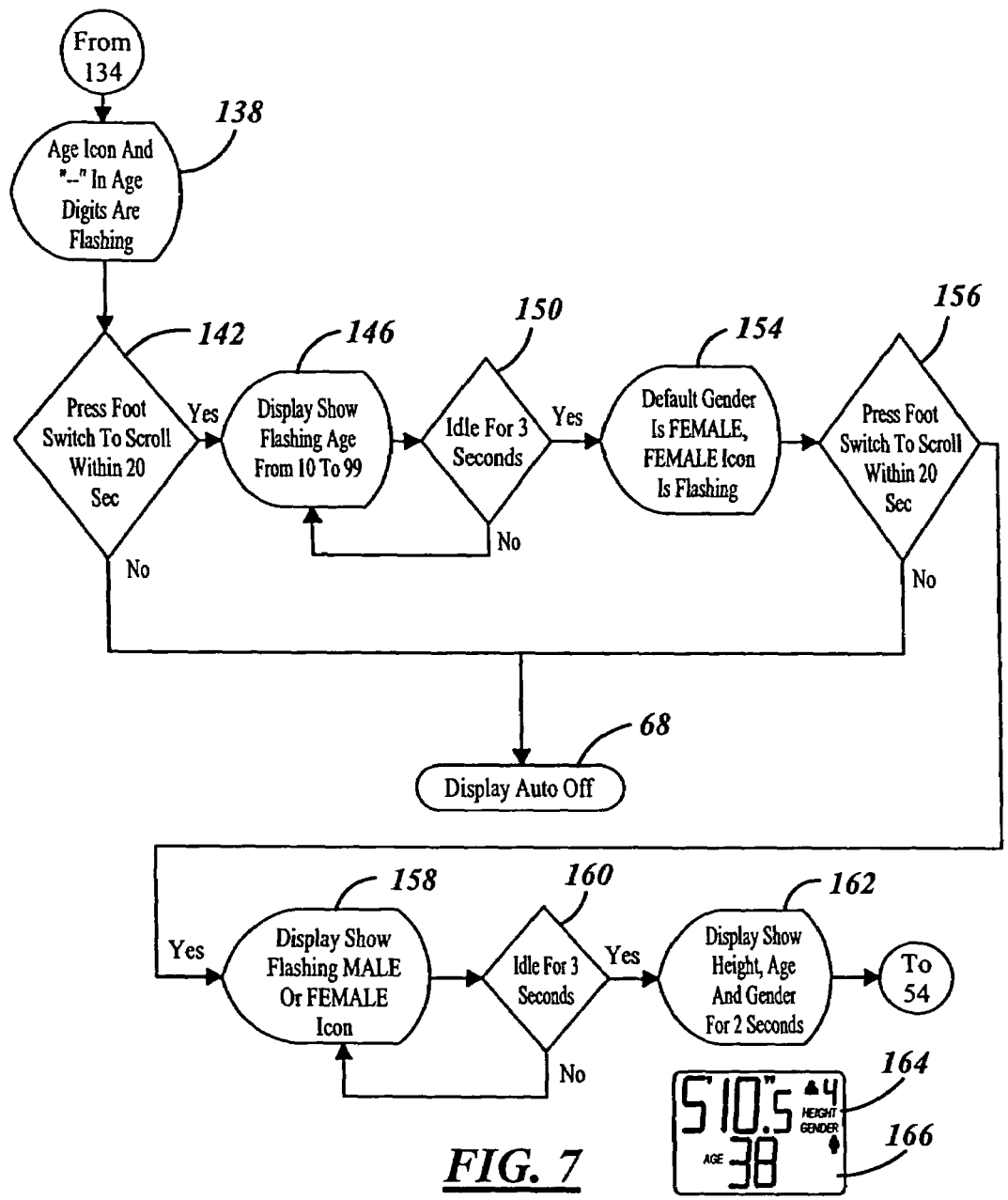

FIGS. 6 and 7 illustrate the programming of the scale 7 in its first time use. For a first use and set up, the user presses their foot on the platform 10 and holds it for at least three seconds (operation 71). The 3-second hold will turn on the scale 7. The display 12 displays a user number 1 as a default message in operation 73. If this is the first user of the scale, the controller processor 16 goes to operation 100 via operation 74 (provided that the user releases their foot from the platform 10 before the expiration of 3 additional seconds in operation 74). If a second identified user of the scale 7 is setting up the scale 7, operations 74, 86, 82, and 84 allow the second user to toggle to the correct user number as previously described.

In operation 100 the user number and icon light up until the setup process is terminated in operation 100. In operation 104, an icon for height and a digit for height in feet flash on the display 12. The user in operation 108 will presses their foot on the scale platform 10 to scroll the display 12 to show a flashing height in feet in operation 114. If the user does not press their foot on the platform 10 after operation 104 within 20 seconds, the controller processor 16 proceeds to an automatic shut off operation 68 via operation 112. After the user takes their foot off the platform 10 for at least three seconds in operation 118, the height in feet is set. The controller processor 16 then causes the display 12 to show inches in operation 122 and in operation 126 the user presses their foot on the scale platform 10 to cause the display 12 to scroll to the proper height in inches in operation 130. If the user does not press their foot on the platform 10 after operation 122 within 20 seconds, the controller processor 16 proceeds to an automatic shut off operation 68. After the user is idle (removes their foot) for three seconds in operation 134 the height in inches is set. The controller processor 16 records this individual unique quality of this identified user in the programmable memory 20.

The controller processor 16 then proceeds to operation 138 wherein the age icon and age digits on the display 12 flash. The user then presses their foot on the platform in operation 142 within 20 seconds to prevent automatic shut off operation 68. The display 12 flashes age in a limit range from 10 to 99 or other suitable numbers in operation 146. When the user is idle (removes their foot from the platform 10) for three seconds in operation 150, the age of the user is set. After the setting of the identified user's age in operation 154, the gender icon will flash. Typically, the gender icon defaults to female. Again, the user must press on the platform within 20 seconds (operation 156) to avoid automatic shut off. After stepping on the platform 10, the display 12 shows the male or female icon in operation 158. If the user is idle for three seconds in operation 160 the display 12 shows the height, age and gender for two seconds in operation 162 in the top row of the display window 12. The set up is complete.

Figure 8:
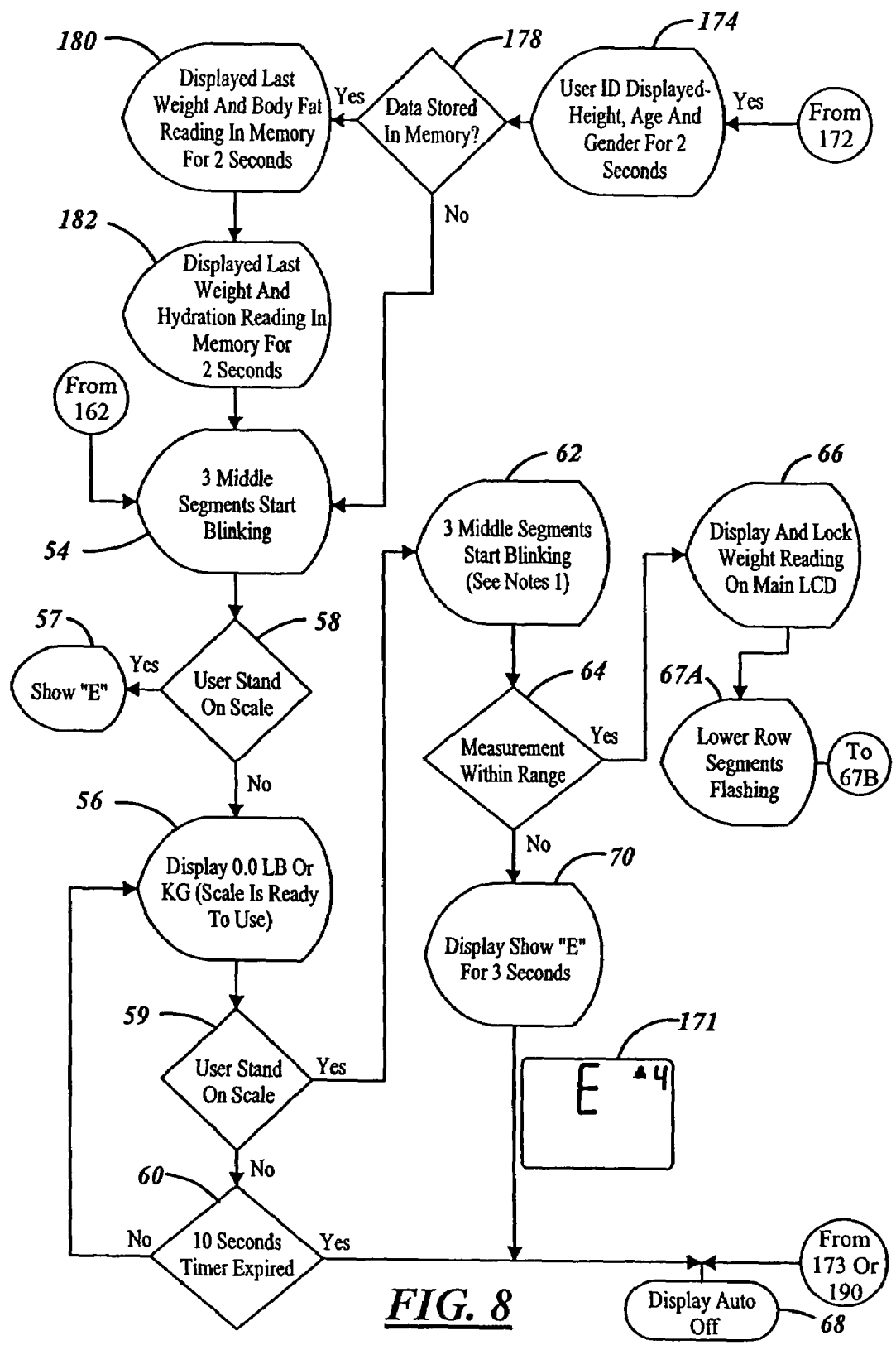
FIGS. 8 and 9 are a process flow chart of the scale of FIG. 1 being operated under a mode of operation providing an identified user's weight and an attribute of the identified user that is both dependent upon the identified user's weight and a unique quality of the identified user.
Figure 9:
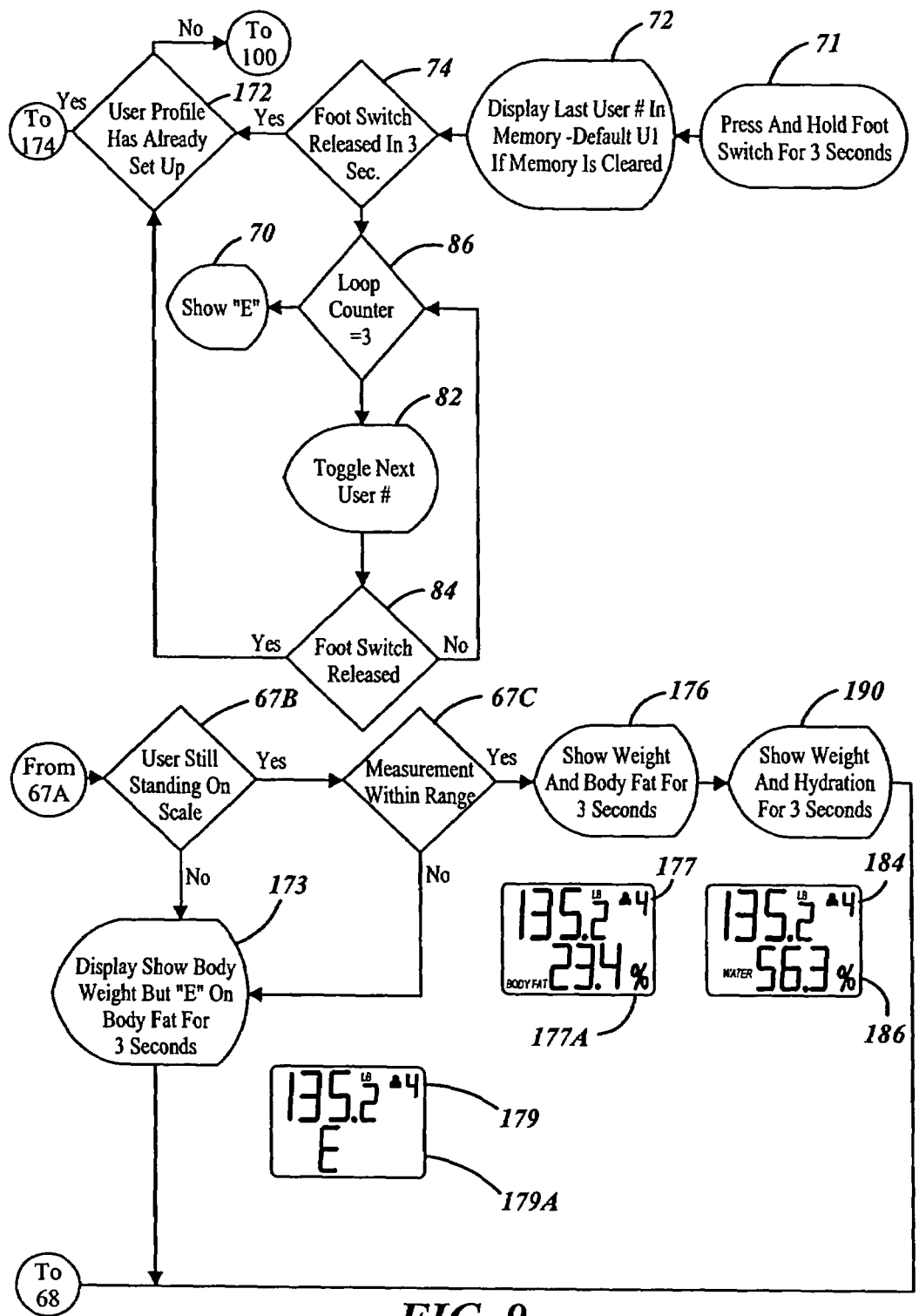
Figure 11:
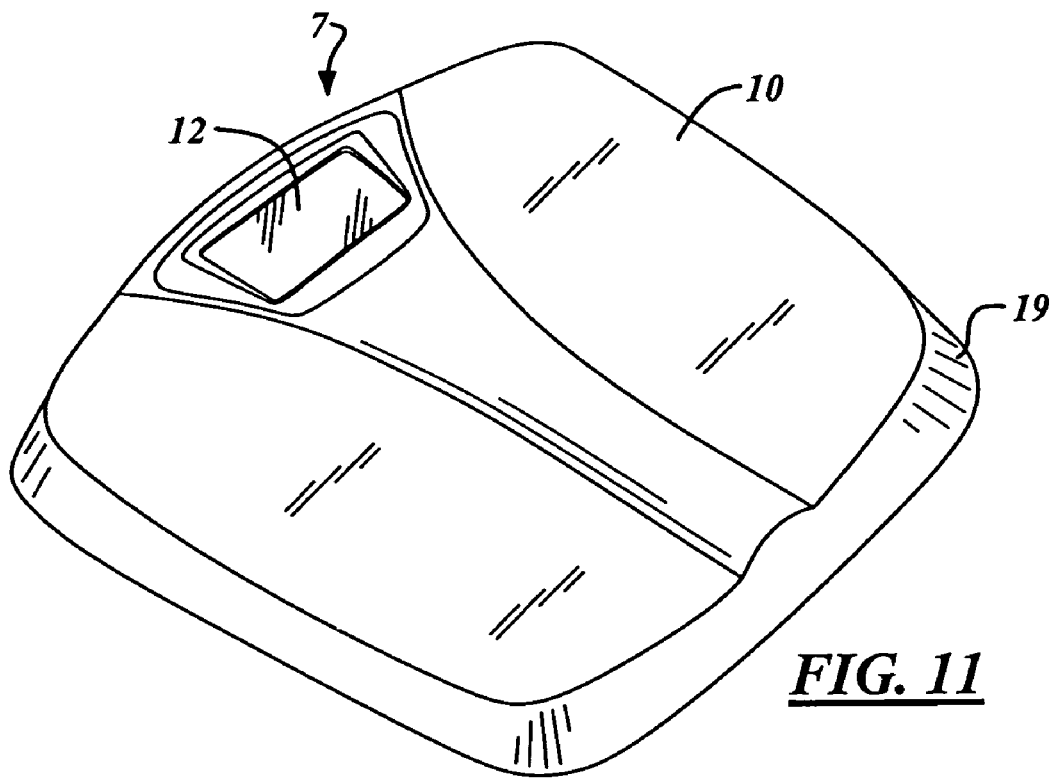
FIG. 11 is a perspective view of the scale shown in FIG. 1.
Figure 12:
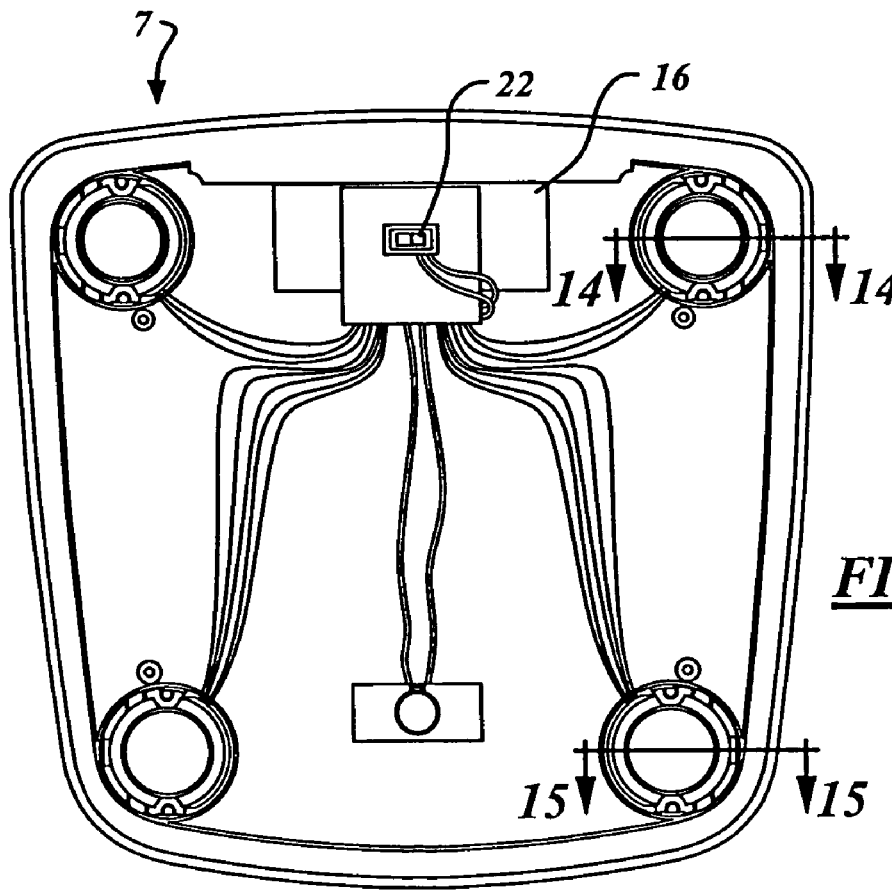
FIG. 12 is a bottom view of the scale shown in FIG. 11.

Referring to FIGS. 8 and 9, a process flow chart for the scale 7 is provided. To place the scale 7 in a mode providing readings of weight and percentages of body fat and water hydration, in operation 71 (FIG. 9), the user presses and hold their foot on the platform 10 for at least three seconds. The display 12 in operation 72 displays the last user in the memory. The default user is user number 1 if the memory is cleared. Again in operation 74 86, 82 and 84 the platform 10 is used to switch to the correct identified user. The controller processor 16 then proceeds to operation 172 to see if the identified user has set up their individual unique qualities or data regarding to age, height, and gender. This inquiry causes the controller processor 16 to query the programmable memory 20. If the identified user has not set up their unique qualities, the controller processor 16 proceeds to operation 100 for set up as previously described. If the identified user has previously set up their unique qualities, the controller processor 16 proceeds to operation 174. In operation 174 the user's ID number, height, age, and gender are displayed for two seconds. The controller processor 16 then proceeds to operations 180 and 182 if there has been a previous weight and body fat recording in the programmable memory 20. If there has been a prior body fat and weight readings, they are displayed for two seconds (operation 180). In operation 182, the last weight and hydration readings are displayed for two seconds. If there is no prior weight and body fat recording for this identified user, the controller processor 16 proceeds directly from operation 178 to operation 54 wherein the three middle segments of the display 12 start to blink.

After operation 54, the controller processor 16 proceeds to operations 58, 56, 59, and 60 as previously described. If the identified user stands on the scale 7, the three middle segments start blinking again in operation 62. In operation 64, the controller processor 16 determines if the weight measurement is within the range or limits of accurate scale reading. The controller processor 16 proceeds to operation 66 wherein the display 12 locks on the weight reading.

The lower row of the display 12 flashes in operation 67A. If the identified user remains on the scale (operation 67B), the controller processor 16 proceeds to operation 176 (assuming an accurate body fat percentage measurement in operation 67C) causing the display 12 to illustrate the weight and body fat for three seconds as shown in as items 177 and 177A. The body fat percentage (and water hydration percentage) is determined from a lookup chart or from a formula in the read only memory 18. In operation 67C there is a check to see if the body fat percentage is within accurate ranges of readings. If the body fat reading is outside of accurate range, the controller processor 16 proceeds to operation 173. In operation 173, the display 12 illustrates weight reading 179 and an "E" error message 179A. The controller processor 16 then goes to shut off under operation 68.

After displaying weight and percent body fat for three seconds, the display 12 in operation 190 displays weight and water hydration percentage for three seconds as shown in the display top row 184 and bottom row 186. After operation 190, the controller processor goes to automatic shut off operation 68.

Figure 5:
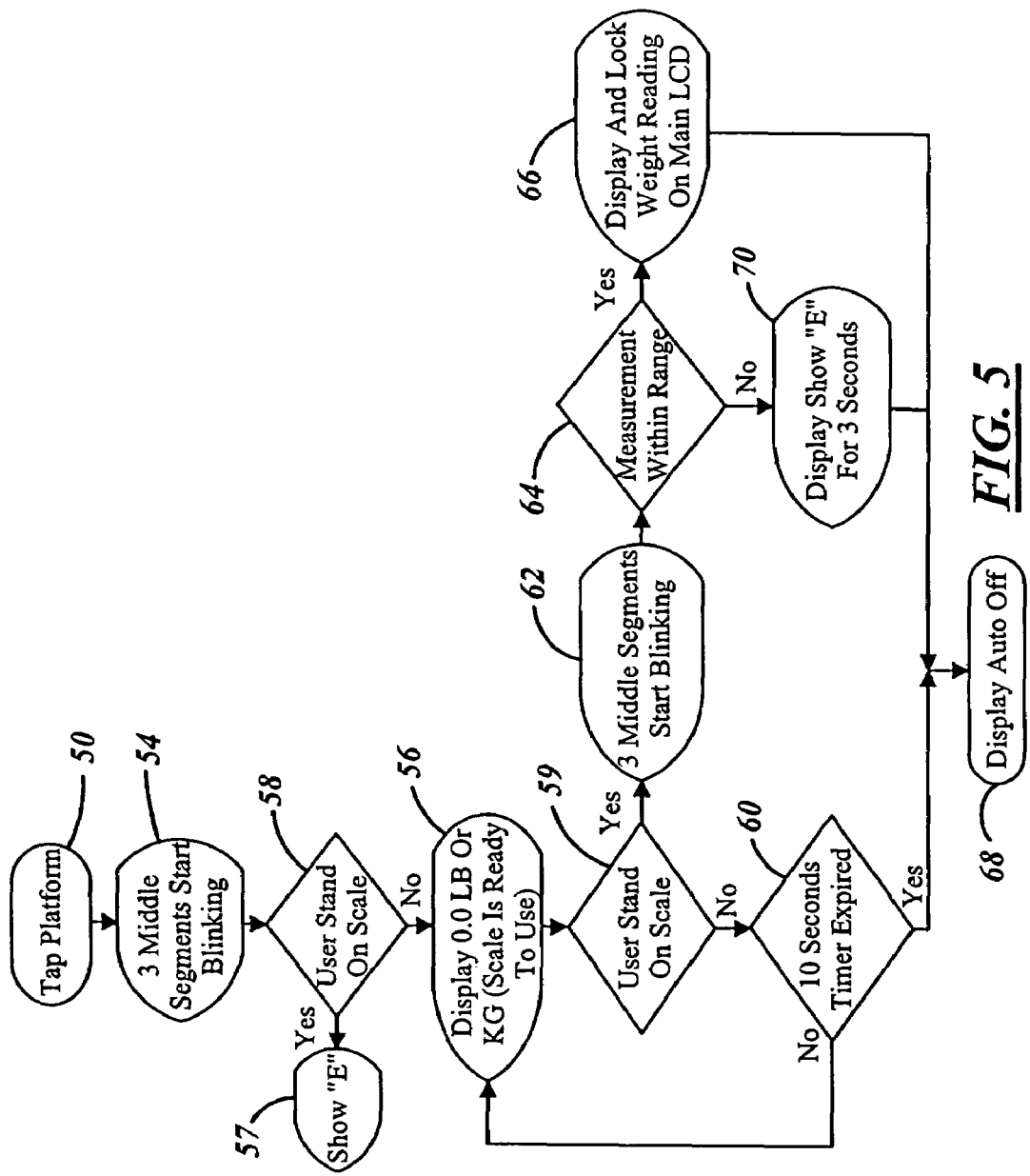
FIG. 5 is a process flow chart of an alternate weight only mode of operation of the scale shown in FIG. 1.

If it is desired that the scale 7 be utilize in the weight only mode of operation, the user turns on the scale 7 by tapping the platform 10 in operation 50 (FIG. 5). The tapping turn on of operation 50 also sets of the scale 7 in the weight only mode of operation. From operation 50, the scale 7 proceeds directly to operation 54. Further processes proceed as previously described for weight only operation for the embodiment described in FIG. 4 with the exception that the delta weight is not provided.

While preferred embodiments of the present invention have been disclosed, it is to be understood it has been described by way of example only, and various modifications can be made without departing from the spirit and scope of the invention as it is encompassed in the following claims.

The invention claimed is:

1. A digital scale comprising:
   a display screen:
   a buttonless top platform;
   a controller operatively associated with said display screen and said platform wherein physical contact with said platform allows a user of said scale to power said scale, determine a mode of operation of said scale, and identify a user of said scale; and
   wherein said controller comprises a plurality of sensors, each of said sensors associated with a corresponding support on an underside of said platform, a processing means for receiving and processing signals generated by said plurality of sensors, and a timing means for determining both the duration of said signals and the duration of displayed inputs and measurements.

2. A scale as described in claim 1 wherein contact with said platform allows an identified user of said scale to input a unique quality of said identified user.

3. A scale as described in claim 1 wherein an identified user is represented by a numeral.

4. A scale as described in claim 1 wherein a first mode of operation of said scale provides a weight only and in a second mode of operation of said scale provides a weight dependent attribute.

5. A scale as described in claim 4 wherein said weight dependent attribute is a delta weight value.

6. A scale as described in claim 4 wherein contact with said platform allows an identified user of said scale to input a unique quality of said identified user and wherein said second mode of operation of said scale provides an attribute that is dependent upon weight and a unique quality of said identified user.

7. A scale as described in claim 6 wherein said attribute is percentage body fat.

8. A scale as described in claim 6 wherein said attribute is percentage water hydration.

9. A scale as described in claim 2 wherein said unique quality is age.

10. A scale as described in claim 2 wherein said unique quality is height.

11. A scale as described in claim 2 wherein said unique quality is gender.

12. A digital scale comprising:
a display screen;
a buttonless top platform;
a controller operatively associated with said display screen and said platform wherein physical contact with said platform allows a user of said scale to power said scale, determine a mode of operation of said scale, identify a user of said scale, and to input a unique quality of said user;
wherein said controller comprises a plurality of sensors, each of said sensors associated with a corresponding support on an underside of said platform, a processing means for receiving and processing signals generated by said plurality of sensors, and a timing means for determining both the duration of said signals and the duration of displayed inputs and measurements; and
wherein said scale has a first mode of operation providing at least a weight and a second mode of operation providing an attribute that is dependent upon a weight of an identified user and a unique quality of said identified user.

13. A method of using a digital scale including, a display screen, a buttonless top platform, and a controller operatively associated with said display screen and said platform wherein contact with said platform allows a user of said scale to power said scale, determine a mode of operation of said scale, identify a user of said scale and input a unique quality of said user, wherein said controller comprises a plurality of sensors, each of said sensors associated with a corresponding support on an underside of said platform, a processing means for receiving and processing signals generated by said plurality of sensors, and a timing means for determining both the duration of said signals and the duration of displayed inputs and measurements, and wherein said scale has a first mode of operation providing at least a weight and a second mode of operation providing an attribute that is dependent upon a weight of an identified user and a unique quality of said identified user, said method comprising:

physically contacting said platform to power on said scale and to determine said operating mode of said scale;
using said platform to identify said user of said scale;
using said platform to input said unique quality of said identified user of said scale;
displaying a weight reading of said user in said first mode of operation or displaying a weight and a weight and unique identified quality dependent attribute reading in said second mode of operation; and
automatically powering off said scale after said reading is displayed.

14. A method as described in claim 13 wherein there is a time delay measured by said timing means after said reading before automatic power off of said scale.

15. A method as described in claim 13 wherein said unique quality is age.

16. A method as described in claim 13 wherein said unique quality is height.

17. A method as described in claim 13 wherein said unique quality is gender.

18. A method as described in claim 13 further including displaying an error message if a weight reading is outside limits of accuracy.

19. A method as described in claim 13 replaying a message to inform a user of said scale that said scale is calibrated.

20. A method as described in claim 19 further including displaying an error message if a user of said scale steps onto said scale if said scale is not calibrated.

21. A method as described in claim 13 wherein physically interacting with said platform turns on said scale and places said places in said first mode of operation.

22. A method as described in claim 13 wherein activating and maintaining activation of at least one of said sensors for a predetermined period of time turns on said scale and places said scale in said second mode of operation.

* * * * *